United States Patent [19]

Goldblum et al.

[11] Patent Number: 5,484,707
[45] Date of Patent: * Jan. 16, 1996

[54] ASSAY FOR FREE SECRETORY COMPONENT AND METHODS FOR MONITORING ORGAN REJECTION

[75] Inventors: Randall M. Goldblum, Dickinson; Srinivasan Rajaraman, Galveston, both of Tex.

[73] Assignee: The Board of Regents, The University of Texas System, Austin, Tex.

[*] Notice: The portion of the term of this patent subsequent to Aug. 23, 2011, has been disclaimed.

[21] Appl. No.: 174,670

[22] Filed: Dec. 28, 1993

Related U.S. Application Data

[63] Continuation of Ser. No. 736,448, Jul. 26, 1991, Pat. No. 5,340,721.
[51] Int. Cl.$^6$ .................... G01N 33/543; G01N 33/566
[52] U.S. Cl. .................... 435/7.92; 424/278.1; 435/7.8; 435/7.94; 435/975; 436/501; 436/513; 436/518; 514/11; 514/885
[58] Field of Search .................... 435/7.8, 7.92, 435/7.94, 975; 436/87, 501, 513, 518; 514/11, 885; 424/278.1

[56] References Cited

PUBLICATIONS

J. Floege et al, Clin. Physiol. Biochem., 7, 165–175, 1989.
C. Vincent et al, Jour. Immunol. Meth., 106, 153–160, 1988.
M. G. Scott, Trends In Biotechnology, 3, 170–175, 1985.
A. Voller, In E. T. Maggio (Ed.) Enzyme Immunoassay, Chapter 9, CRC Press, Inc., Boca Raton, Fla., 1980, pp. 181–196.

*Primary Examiner*—David Saunders
*Attorney, Agent, or Firm*—Arnold, White & Durkee

[57] ABSTRACT

Methods of monitoring and detecting the early onset of organ injury incident rejection of a organ rejection in an animal are disclosed. The described methods are capable of distinguishing organ rejection injury from other organ tissue damage in the animal. Free secretory component levels in an animal biological fluid (e.g., bile, urine, blood, amniotic fluid) may be used to identify organ rejection in an animal. Multiple and single organ transplant patients may be monitored and diagnosed according to the claimed methods. Biological fluids, such as blood, (serum) or urine, are analyzed immunologically using a particularly adapted ELISA which are then compared to an FSC control concentration to identify elevated FSC values. Animals with test FSC above FSC control concentrations are diagnosed as having an ongoing organ rejection episode. The detection of congenital renal dysfunction in utero is also provided according to the present invention through the measurement of FSC in the amniotic fluid. The described methods are specific for indicating organ rejection tissue injury, and distinguish kidney rejection tissue injury, in particular, from other causes of kidney injury, such as cyclosporin toxicity, urinary tract infection, and urinary obstruction and toxicity (incident to immunosuppressive therapy with cyclosporin). A kit for use in the identification of an organ rejection episode in a patient through measurement of FSC in a biological sample is also provided.

17 Claims, 2 Drawing Sheets

ASSAY FOR FREE SECRETORY COMPONENT AND METHODS FOR MONITORING ORGAN REJECTION

The United States Government may have rights in the present invention as relevant developmental work was supported by a National Institutes of Health (NIAID) RO1 Grant No. AJ21412 and pursuant to a contact with NICHD (#6-918) HD 62918. This is a continuation of application Ser. No. 07/736,448 filed Jul. 26,1991 and now U.S. Pat No. 5,340,721.

BACKGROUND OF THE INVENTION

1. Field of the Invention

The present invention relates generally to the field of diagnostic medicine, most particularly, to the field of methods for diagnosing organ graft rejection. The invention relates to methods for monitoring and detecting organ rejection in a patient through immunodiagnostic assays which measure free secretory component (FSC) in a biological sample.

In that particular embodiments of the present invention relate to the measurement of FSC in a urine sample, the field of the present invention also relates to urine sample analysis for the detection of organ rejection. In most preferred embodiments of the described invention, a method[ for monitoring and detecting allograft rejection is provided through the monitoring of urine concentrations of the glycoprotein free secretory component. The described invention most particularly relates to the field of methods for detecting renal allograft rejection, as the procedures disclosed herein are capable of distinguishing renal allograft rejection from other form; of renal and extra renal problems in kidney transplant patients.

The present invention also relates to the field of diagnostic assay kits, as a diagnostic kit for use in the screening of kidney transplant patients to detect early kidney rejection is provided.

2. Description of the Related Art

Approximately 10,000 kidney transplants are performed annually in the United States. Despite the availability of potent immunosuppressive agents, graft rejection remains the main complication of renal transplantation. For example, approximately 50% of all renal allograft recipients are thought to suffer at least one episode of graft rejection. The likelihood of kidney loss due to rejection is highest during the first year post transplant (10–20%), but a small proportion (3–5%) of kidneys are rejected each year even after that[1].

The statistics indicate that graft rejection is often not detected early enough in the rejection episode to allow initiation of countervailing treatment, which would effectively halt the rejection process, in time to prevent the organ rejection. A method for the early detection of graft rejection would thus be an important clinical tool for maintaining the viability of a transplanted organ through early detection in the rejection process. The clinician would thus be provided an opportunity to administer immunosuppressive agents to the patient at a time when the rejection process could be effectively halted and/or prevented altogether.

The diagnosis of acute allograft rejection is classically based on the presence of one or more symptoms. For example, symptoms of acute allograft rejection include weight gain, reduced urine output, increased serum creatine concentrations, hypertension, fever, and graft enlargement and tenderness. However, the use of these symptoms alone to detect rejection is not adequate. Currently, most transplant rejection episodes are detected by measuring periodically the function of the transplanted kidney, for example by using biochemical tests such as assays which measure serum creatine concentrations alone.

Other non-invasive methods for detecting renal graft rejection are under investigation, and depend primarily on the measurement of "indicators" of activation of the immune system. For example, the quantification of T-lymphocyte subsets[2] or soluble T-cell surface receptors (e.g., interleukin 2 receptor)[3] in the blood have been used to monitor graft rejection.

Unfortunately, other complications of the transplant procedure, including urinary tract infection, urinary obstruction and toxicity of the immunosuppressive therapy itself (particularly with cyclosporin A), often mimic the clinical and/or laboratory findings of graft rejection. For example, kidney toxicity to cyclosporin A (a drug used to prevent rejection of kidneys) often results in elevated levels of creatinine in the serum and adenosine deaminase binding protein in urine. The measurement of these constituents would therefore fail to distinguish kidney rejection per se from toxicity to the immunosuppressive agents used to prevent rejection. Such would render false positive results for graft rejection in a patient. In addition, other unrelated illnesses can produce clinical and laboratory findings which resemble those of renal transplant rejection. For instance, T-cell activation may occur during common viral infections as well as during episodes of renal allograft rejection[4], again lending to the occurrence of false positive laboratory results in a patient.

In addition, many abnormalities of the kidney are reflected in changes in the volume and composition of the urine. Therefore, urine tests might provide a more direct and therefore specific, indication of renal allograft rejection than assays for components included in the blood. Measurement of renal tubular and serum proteins in the urine, including β-2 microglobulin[5,6], gamma glutamyl trans-peptidase[6], N-acetyl-β-D-glucosaminidase[7,8], adenosine deaminase-binding protein[10,11] (produced by proximal nephron), complement components, and lysozyme[4,9] have all been proposed. However, none of these markers have been shown to distinguish the injury from renal allograft rejection apart from other renal injuries.

Presently, renal biopsy remains the most definitive test to specifically diagnose renal allograft rejection. However, this method has major limitations. For example, since the biopsy procedure itself has complications, and since a portion of the renal transplant is removed during each biopsy, transplant biopsy cannot be performed on a routine or even frequent basis to monitor renal allograft rejection. In addition, the invasive nature of a renal biopsy is both uncomfortable and inconvenient for patient subjects. Accurate interpretation of the renal transplant biopsy also demands the expertise of a pathologist with extensive experience in analyzing a biopsy sample for evidence of renal transplant rejection. Hence, renal biopsies are reserved for those patients that demonstrate other clinical and/or laboratory evidence of renal allograft rejection limiting its use or potential use in detecting early graft rejection.

While no direct evidence for the induction of secretory component in kidney cells by injury is known to exist, one immunohistologic study of renal autopsy tissue demonstrated that secretory component was much more prominent in the distal tubules when renal disease was present[28]. The present inventors have recently examined a representative number of biopsies from renal allografts from patients undergoing graft rejection, and compared these to biopsies from patients with cyclosporin toxicity, using immunofluorescence assays with monoclonal antibodies to secretory component. From these preliminary observations, the inventors found that kidneys undergoing rejection expressed much more secretory component in their distal tubules compared to kidneys from patients with cyclosporin toxicity (unpublished data). The inventors therefore propose a never-before-described method for discerning kidney rejection in patients receiving immunosuppressive agents such as CSA, by monitoring urinary free secretory component. Concentrations of FSC are not observed to increase with the administration of immunosuppressive drugs (or reactions thereto), thereby essentially eliminating false positive results for kidney rejection.

Secretory component is an 80,000 molecular weight fragment of an integral (trans) membrane glycoprotein, termed "polymeric immunoglobulin receptor" (PIgR). PIgR is synthesized by secretory epithelial cells which line the mucosal surfaces of the body[12,13]. It mediates binding, endocytosis and vectorial transport of polymeric IgA (pIgA), and to a lesser extent IgM[14], from the basal lateral to the apical surface of the epithelial cell[15-19]. Here, the PIgR is proteolytically cleaved near the outside surface of the epithelial cell[20,] releasing the N-terminal segment, termed secretory component (SC).

The secreted secretory component, complexed with pIgA, is termed "secretory IgA" (sIgA)[12]. In this complex, secretory component is thought to protect the IgA from proteolytic cleavage. The large amounts of sIgA found in saliva and gastrointestinal secretions, lung secretions, cervicovaginal secretions, breast milk, and tears are thought to constitute the first line of immunological defense against some mucosal infections. The smaller amount of sIgA found in urine may also help protect against urinary tract infection[22].

When secretory component is secreted from the epithelial cell without any immunoglobulin attached, it is termed free-secretory component (FSC). FSC has also been reported in all external secretions in smaller amounts[23]. The exact function of FSC remains unknown. It is hypothesized that the synthesis of secretory component in some tissues may be regulated by hormones[24,] and other soluble mediators, such as cytokines involved in inflammation. In cultured colon carcinoma cells, the cytokines interferon gama and tumor necrosis-α and interleukin-4, alone and in combination, have been shown to increase the production and release of secretory component.[25-27]

The term "secretory component", as used in describing the present invention, refers to either the conjugated (sIgA-associated) or unconjugated (FSC) form of the secretory component molecule. Free secretory component (FSC), as used in describing the present invention, refers only to the free, unconjugated form of the secretory component molecule.

Since secretory component is normally secreted from the luminal surface of epithelial cells, the inventors hypothesize that it is likely that increased production of secretory component in the kidney will increase excretion of sIgA and/or secretory component in the urine. A recent study quantified sIgA by ELISA in the urine of patients with a variety of renal disorders[29]. Compared to healthy subjects, patients with IgA nephritis and other forms of chronic glomerulonephritis had elevated urinary sIgA. Urinary sIgA levels were only slightly increased in heavy proteinuria. Additionally, the highest concentrations of urinary sIgA (22-fold above normal) were found in patients with urinary tract infections. Renal allograft recipients with stable graft function had urinary sIgA levels that were only slightly increased above those of normal individuals. These results suggest that urinary sIgA production is enhanced by renal inflammation, perhaps due to induction of local secretory component and/or IgA production.

Urinary free secretory component (FSC) excretion, (unconjugated secretory component) has not been studied as extensively. As will be recalled, FSC (or free secretory component) is produced by the distal nephron. It has been observed that the level of expression and excretion of FSC may be increased by renal inflammatory reactions like infection[28] or allograft rejection, as well as by tubular injury. One recent study demonstrated that urinary FSC did not differ between persons with acute/recurrent urinary tract infections, and normal controls.[32] Nor did urinary FSC levels differ between patients with IgA deficiency and age and sex-matched normal adult control subjects.[32]

A major characteristic of the secretions that protect mucosal surfaces is that they contain products of the polymeric immunoglobulin transport system, namely secretory immunoglobulins (sIgA and sIgM) and free secretory component (SC). SC expression has even been demonstrated as present in fetal tissues. For example, by the seventh week of gestation, even before the fetus is able to produce Ig, SC has been detected in fetal tissues.[4] Free SC (free secretory component) has been observed by the inventors in human amniotic fluid. Based on reactivity with antisera to secretory component, the IgA of amniotic fluid is thought to be sIgA immunoglobulin containing secretory component[33].

Amniotic fluid is known to serve as an immunological barrier between the fetus and maternal external environments, thereby protecting against intrauterine infections. As already noted, amniotic fluid has been reported to contain low levels of sIgA and other proteins typical of external secretions, but these proteins are not usually considered. an immunologic secretion[4]. Thus, the role and sources of the various forms of secretory component (SC) in amniotic fluid have not yet been completely characterized.

The present inventors have found that the concentration of SC in amniotic fluid (AmF) varies with the gestational age of the fetus. Additionally, the inventors have found that most of the SC in human AmF exists in its free form (FSC). In this regard, the inventors observed that amniotic: fluid from full term pregnancies contained FSC in concentrations comparable to other external secretions, such as saliva or bile[42].

The fetal urogenital system and the amniotic membrane have been demonstrated to contribute to FSC levels and sIgA levels in amniotic fluid. Given those observations already collected by the inventors and others regarding FSC and SC in fetal tissues and AmF, the inventors propose a method for monitoring fetal kidney abnormalities through monitoring fetal secretory component levels in amniotic fluid. For example, this proposed method may be used to monitor the disease known as Potter's Syndrome (a disorder characterized by abnormal fetal kidney development). Detection of kidney malfunction early in pregnancy by monitoring AmF levels of FSC would provide an extremely valuable diagnostic tool for following fetal kidney development. Once detected, the kidney-malfunctioning fetus might be treatable by the clinician and alert the patient to the condition.

A simple, non-invasive method for rapid detection of kidney and other organ rejection episodes would have the dual advantage of requiring no venipuncture or biopsy and further allowing testing at virtually any clinic or office remote from actual transplantation medical centers. More specifically, a urinary FSC test to monitor kidney rejection as a screening procedure would have practical utility as an initial non-invasive procedure that would quickly alert the physician of the need for further, more extensive and/or patient involved evaluation and treatment. Quantification of urinary FSC may also be useful in distinguishing inflammatory renal disease (rejection or infection) from renal toxicity precipitated from immunosuppressive drugs, such as cyclosporin A.

A simple, non-invasive diagnostic test which could serve as an initial screening procedure for detecting renal transplant rejection, or could distinguish rejection from other diseases that produce the same symptoms and biochemical changes, could improve greatly the prognosis of patient kidney transplant recipients. As allograft rejection can often be treated effectively if detected early, the availability of an effective screening test for early graft rejection detection which could be performed conveniently on a relatively frequent periodic basis would potentially improve the survival of both the transplanted organ, and the transplant patient. Ultimately, such a test could also reduce the high cost of treating chronic renal failure.

SUMMARY OF THE INVENTION

The present invention provides a simple, rapid and specific method for monitoring and/or identifying organ rejection in an animal. It is contemplated that the present methods may be advantageously employed in the detection of both single organ rejection as well as multiple-organ rejection (such as the liver, kidney, lung or pancreas or any combination thereof) in a transplant patient. The most preferred application of the described methods relate to the detection and monitoring of the rejection of kidney allografts in an animal.

Allograft, as that term is used in the present application, refers to an organ which is transplanted into an animal of the same species as the organ donor. The described methods alert of an ongoing organ rejection episode through the detection of an elevated or otherwise abnormal concentration of free secretory component in a biological sample from the animal. The detection of elevated free secretory component levels in the animal above concentrations characteristic of a defined "control" FSC concentration of a like-biological fluid, such as from a transplanted animal without previous episodes of graft rejection, will identify an ongoing organ rejection in the animal.

Even more particularly, the present invention provides methods whereby renal tubular inflammation, specifically the tubular inflammation attendant renal allograft rejection, is determined based on quantification of the glycoprotein free secretory component (FSC, also termed free secretory component of IgA and polymeric immunogobulin receptor) in the voided urine of renal allograft recipients.

The diagnostic value in monitoring human renal transplant patients by the measurement of FSC concentrations is indicated by data generated by the inventors which shows that FSC concentration in urine is greater in patients admitted to a renal transplantation unit for suspected graft rejection than in non-renal transplant control patients. The concentration of urine FSC also has been demonstrated to fall rapidly in some patients after their medicinal regimen has been changed. This indicates to the present inventors that urine FSC measurements may also be used as a signal of when a change in treatment is reversing rejection of a grafted organ.

The present invention most particularly provides a non-invasive method for identifying organ injury incident to organ rejection in an animal, the method comprising first obtaining a biological sample from the animal having an organ transplant; measuring a concentration of FSC in the biological sample to provide an FSC test concentration; comparing the FSC test concentration to a control FSC concentration characteristic for the biological sample; and identifying an organ injury incident to organ rejection in an animal having an FSC concentration greater than the FSC control concentration.

Most preferably the biological sample used to determine the control FSC value should be the same type of biological sample obtained from the "test" animal. For example, where the animal sample obtained is a urine sample, a reference control value of FSC should be determined from a urine sample obtained from an animal(s) having had an organ transplant with no prior known episodes of organ rejection, from an animal(s) with no organ transplant or from an autologous urine sample obtained from the animal prior to any incidence of any organ rejection episode.

The present inventors have found that FSC concentrations will vary as between types of biological fluids/secretions, such as urine, bile, bronchial secretions, milk, serum and amniotic fluid. Any one of these biological fluids may be used for the purpose of measuring FSC concentration. Most preferably, the biological fluid for test and control FSC determinations is urine. Most preferably, in both the method for inhibiting a kidney transplant rejection, identifying a renal allograft rejection episode and for distinguishing renal allograft rejection injury from renal non-allograft injury in a kidney transplant recipient, the FSC control concentration and FSC test concentrations are normalized as against the creatinine concentration of the biological sample.

A control FSC concentration of a biological sample may be determined from an autologous biological sample obtained from the patient prior to any evidence or incidence of an organ rejection episode. Alternatively, the control free secretory component concentration may be determined as an average of a representative number of like-biological samples obtained from a control population of animals. The control reference population may comprise a representative number of non-transplant animals, or a representative number of animals having had an organ transplant of the same organ as the animal under observation with no prior episodes of organ rejection.

The present invention is expected to provide a noninvasive and economical method for frequently monitoring the efficacy of a transplant recipients immunosuppression therapy regimen, as well as for monitoring the status of an organ (e.g. kidney) transplant in the transplant recipient. The rejection/monitoring of a number of different organs may be accomplished, using the described noninvasive method. By way of example, organs which may be monitored according to the methods described herein include a liver, kidney, lung or pancreas grafted organ or tissue. In a preferred embodiment, the described methods are employed to monitor/detect kidney organ rejection in a human.

The ability to provide early detection of ongoing transplanted organ rejection episode will facilitate early patient treatment, enhancing the success of preventing incipient transplant rejection. The increasing shortage of organs available for transplant, and the difficulties associated with obtaining an initial histocompatible organ-donor, highlight the important feature of the claimed invention for improving the success rate of organ transplant as a treatment. Thus, organ rejection as a major risk associated with organ transplant, and may be virtually eliminated through early detection and subsequent prompt and effective immunosuppressive clinical intervention employing the methods of the present invention.

Measurement of FSC in a urine sample as a method to identify or inhibit an ongoing renal allograft rejection episode, in particular, has not to the inventors knowledge been reported in the literature. Various components in urine, such as renal, tubular and serum proteins, including the β-2-microglobulin,[5,6] γ-glutamyl trans-peptidase[7], N-acetyl-β-d-glucoseaminadase[8,9] adenosine deaminase binding protein[11] and complement component and lysozyme[10] have been measured. However, none of these substances have been shown to distinguish renal allograft rejection from other forms of extra-renal or kidney injury (e.g., cyclosporin toxicity).

A method for distinguishing renal injury resulting from allograft rejection and other forms of renal injury is an important further feature of the claimed invention, since increasing a patient's immunosuppressive therapy inappropriately can worsen other conditions attendant the specific renal injury, and further increase other complications attendant the therapy.

The present invention provides a method whereby an ongoing organ rejection episode may be determined by immunological analysis of any of a variety of biological fluids, including urine, bile, amniotic fluid, and bronchial secretions, serum as well as other biological fluid secretions. Most preferably, the present methods may be used in conjunction with a urine sample (in the case of testing for kidney injury the result of allograft organ rejection). In a second most preferred embodiment, the presently disclosed methods may be used in conjunction with amniotic fluid (in the case of a diagnostic test for fetal renal dysfunction).

As a method for inhibiting kidney transplant rejection in an animal with a kidney transplant, the method comprises the steps of first obtaining a urine sample from the animal at periodic intervals after the kidney is transplanted, measuring FSC concentrations in each urine sample of the animal to provide test sample FSC concentrations; determining a control FSC urine concentration; identifying an elevated FSC test concentration in a test sample having an FSC concentration greater than the control FSC urine concentration; classifying an animal having an elevated concentration of FSC as undergoing a kidney rejection episode; and treating the animal undergoing a kidney rejection episode with a regimen of immunosuppressive agents to inhibit kidney transplant rejection in the animal.

A control free secretory component concentration may be determined from a control reference population which may comprise a group of organ transplant recipients with no prior history of episodes of organ rejection or from non-transplant patients of similar age and sex.

As a method for identifying a renal allograft rejection episode in a kidney transplant patient, the present invention in a particularly preferred embodiment comprises first obtaining a patient urine sample from the transplant patient, determining the FSC concentration in the patient urine sample to provide an FSC test concentration; determining an FSC urine concentration from urine samples of non-kidney transplant patients to provide an FSC control concentration; comparing the FSC test sample concentration to the FSC control concentration; and identifying a renal allograft rejection episode in the kidney transplant patient when an FSC test concentration is greater than the FSC control concentration. While the concentration of FSC in the biological sample may be determined by several methods, the most preferred method for measuring the concentration of FSC in a urine sample, for example, is by an enzyme linked immunosorbent assay (ELISA).

An immunological method most preferred for use in the present invention for the measurement of free secretory component (FSC) in virtually any biological fluid is the ELISA (enzyme linked immunosorbent assay), which has been modified in particular aspects for the purposes of the present invention. One feature of the modified ELISA includes the capability of measuring FSC at extremely low concentrations in a biological sample (5 μg/ml).

Identification of a potentially pathologic concentration of FSC is determined on the basis of a comparative testing scale, wherein the test sample FSC concentration is judged to be "elevated" or "normal" as against a baseline control concentration value characteristic of the particular biological fluid being measured. For example, where the biological fluid is a human adult male voided urine sample, the characteristic baseline control concentration of FSC is about 1 μg/ml. This value was calculated as a mean FSC value of 15 non-kidney transplant voided urine samples from adult male human subjects. In contrast, the mean urine FSC concentration value for 15 kidney transplant patients having a history of at least one episode of renal rejection was determined to be about 25 μg/ml.

A characteristic baseline FSC control value may be derived from either an autologous, pre-rejection episode biological sample level, or from a control population of biological samples, such as from a representative number of non-transplant patient samples, or a representative number of transplant patient samples from patients who had received a transplanted organ but who had not demonstrated any previous episodes indicating organ rejection.

Identification of a potentially pathogenic organ rejection episode may also be made on the basis of relative levels of FSC/creatinine in the test sample compared to controls. An average FSC/creatinine ratio, as determined from a control population of urine samples from non-transplant adult human patients, was about 1.04 μg FSC/mg creatinine, the range being between 0.19–3.38 μg FSC/mg creatinine (Table 3). A normal FSC/creatinine range of between 0.32–2.5 μg FSC/mg creatinine was therefore determined for non-transplant, control patient urine samples. In contrast, the range for FSC creatinine in renal transplant patients who had no biopsy evidence of renal allograft rejection is about N.D.–26 μg FSC/mg creatinine (N.D.=non-detectable levels with ELISA assay). Two of 5 patients had some FSC/creatinine values greater than 2.5 μg/mg creatinine. However, 6 patients with renal biopsy evidence of kidney rejection had a range of N.D.–94 μg FSC/mg creatinine. All 6 of these patients had values greater than 2.5 μg/mg creatinine during their hospitalization.

The presently disclosed methods are also exquisitely specific for distinguishing kidney injury from allograft rejection from other non-allograft kidney damage. Thus, a method for distinguishing renal allograft rejection kidney injury from non-allograft kidney injury in a kidney transplant patient is provided as one particularly preferred embodiment of the claimed invention. As a method for distinguishing renal allograft rejection from non-allograft kidney injury in a kidney transplant patient, the method comprises the steps of first obtaining a urine sample from the kidney transplant patient with a form of kidney injury, determining a FSC concentration in the patient urine sample to provide an FSC test concentration, determining an FSC control concentration from a urine sample obtained from a reference control population having no prior history of renal allograft rejection to provide a FSC control concentration; and comparing the FSC test sample concentration to the FSC control concentration; wherein an FSC test concentration greater than the FSC control concentration indicates a renal allograft rejection in the kidney transplant patient and wherein an FSC test concentration the same as or less than the FSC control concentration indicates a non-allograft renal injury.

A control or baseline urine free secretory component (FSC) concentration may be determined as from any of the described control populations (i.e., autologous pre-rejection episode FSC biological sample concentration, or control reference population FSC concentration from a non-transplant population of biological samples or a population of like-organ transplant recipients with no prior history of a graft rejection episode).

In the above described method for distinguished organ rejection kidney injury from other kidney injury, an animal having a form of kidney injury may be identified in a kidney transplant patient having an elevated level of a marker selected from the group consisting of: $\beta$-2 microglobulin; gamma glutamyl trans-peptidase, N-acetyl-$\beta$-D-glucosaminidase; adenosine deaminase-binding protein, complement component; and lysozyme.

The present methods and techniques are also postulated to constitute an effective method for monitoring graft-verses-host disease. In particular, the measurement of FSC in a bone-marrow transplant patient biological sample to detect rejection of epithelial tissue is described herein. Accordingly, a patient sample, most preferably a blood serum sample, would first be obtained, and the concentration of FSC therein determined and compared to an FSC control concentration (measured from a control sample of serum). Most preferably, the FSC control concentration is determined from serum samples obtained from patients who had not received a bone marrow transplant.

Other renal conditions, including renal inflammation such as renal infection, kidney rejection or renal tubular injury, may be monitored through periodic measurement of an animal's urine FSC concentration. As a method for detecting renal inflammation in an animal, the method comprises the steps of obtaining a urine sample from the animal, determining the concentration of glycoprotein free secretory component in the animal urine sample and comparing the concentration of glycoprotein free secretory component in the animal sample to a control concentration of free secretory component, wherein a concentration of glycoprotein free secretory component in the animal sample higher than the control concentration of glycoprotein free secretory component indicates renal inflammation in the patient. This method is most particularly envisioned as suitable for detecting renal allograft related inflammation in a human.

Disclosed also is a method for monitoring fetal renal dysfunction. Such is to be accomplished by monitoring amniotic fluid levels of FSC. Particularly, the condition known as Potter's Syndrome (a condition characterized by the malformation of the fetal kidney) may be identified in the fetus of a pregnant patient where the amniotic fluid FSC concentration is diminished. A concentration of amniotic fluid FSC less than a control concentration of FSC from fluid amniotic obtained from pregnancies of similar gestational ages, would be indicative of fetal renal dysfunction, most particularly Potter's Syndrome, in a human fetus. Again, FSC levels are most preferably determined by a modified ELISA, such as the assay described herein.

A kit for use in the detection of graft rejection is also provided. The kit includes a carrier means adapted to receive at least one multiwell assay plate and at least three container means. One container means preferably includes a volume of free secretory component, with a second container means most preferably comprising an enzyme-conjugated antibody having binding affinity (specificity) for free secretory component antigen and a third container means comprising a receptor ligand capture reagent. In a most preferred embodiment of the kit, the antibody is a monoclonal antibody 6Gll and the receptor ligand capture reagent is an anti-secretory component antibody bound to an enzyme, such as polymeric IgA or IgM conjugated to an enzyme, such as horseradish peroxidase.

The kit may also optionally include a diluent solution with a stabilizing ingredient. By way of example, such a diluent may be a borate or phosphate buffered saline buffer. The FSC employed in the present invention to be used in ELISA assay (i.e., preparing a standard curve, etc) is most preferably FSC derived from human milk. One particular method by which FSC may be derived from human milk is described by Mach[35], which reference is specifically incorporated herein by reference for this purpose.

The following abbreviations are used by inventors throughout the description of the present invention:

ELISA=Enzyme linked immunosorbent assay

FSC=Free Secretory Component

IgA=Immunoglobulin A

N.D.=Non-detectable concentration of measured components in a biological sample using an ELISA assay SC=Secretory Component, conjugated or unconjugated form sIgA=Secretory IgA; conjugated form of SC AmF=Amniotic fluid

DETAILED DESCRIPTION OF THE PREFERRED EMBODIMENTS

Figure 1:
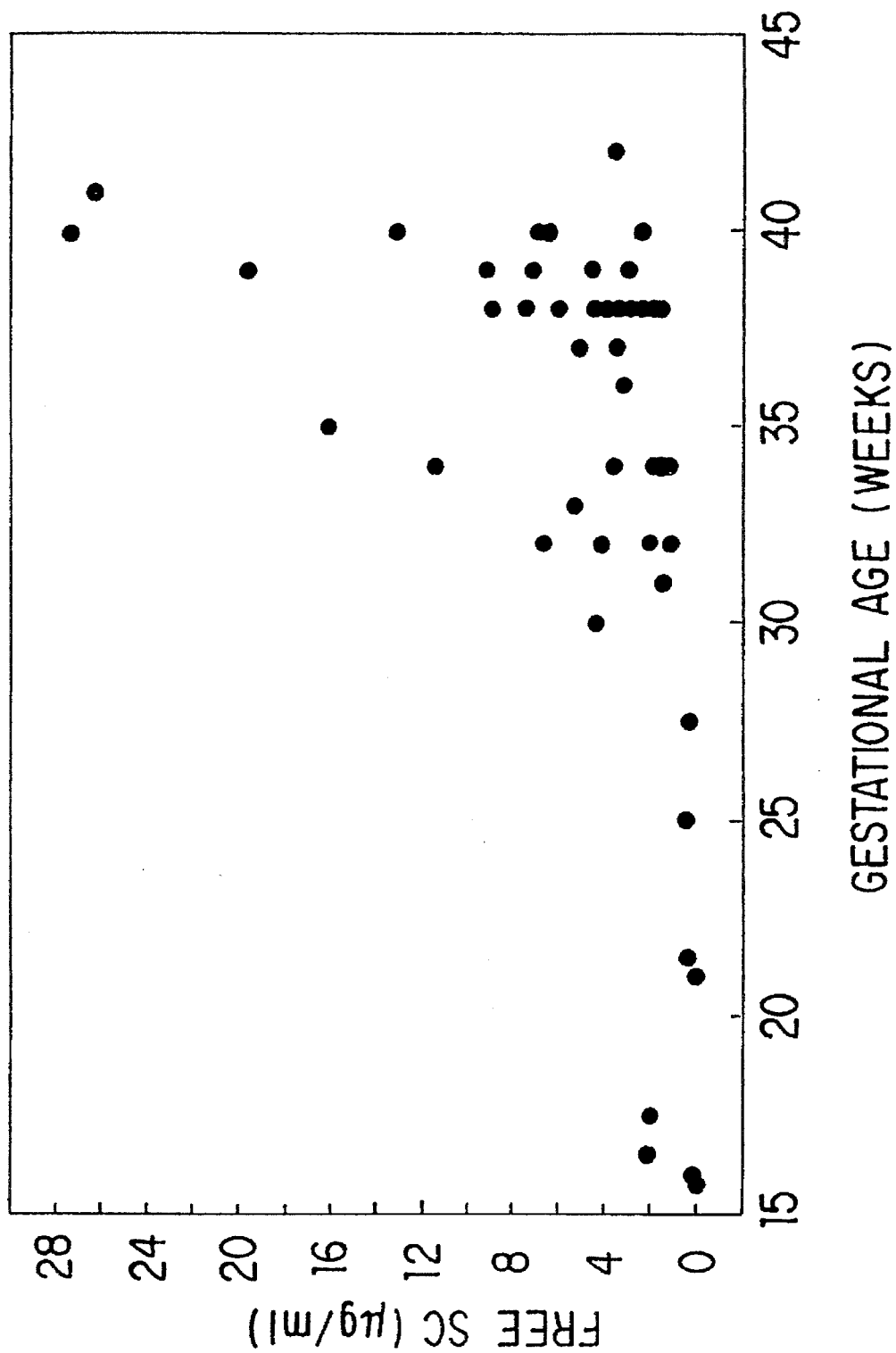
FIG. 1: Scatter Plot of free SC levels in amniotic fluid during gestation. Amniotic fluid samples taken at various gestational ages were assayed for free SC content by quantitative ELISA. Points on the scatter plot represent the level of free SC in individual samples.
Figure 2:
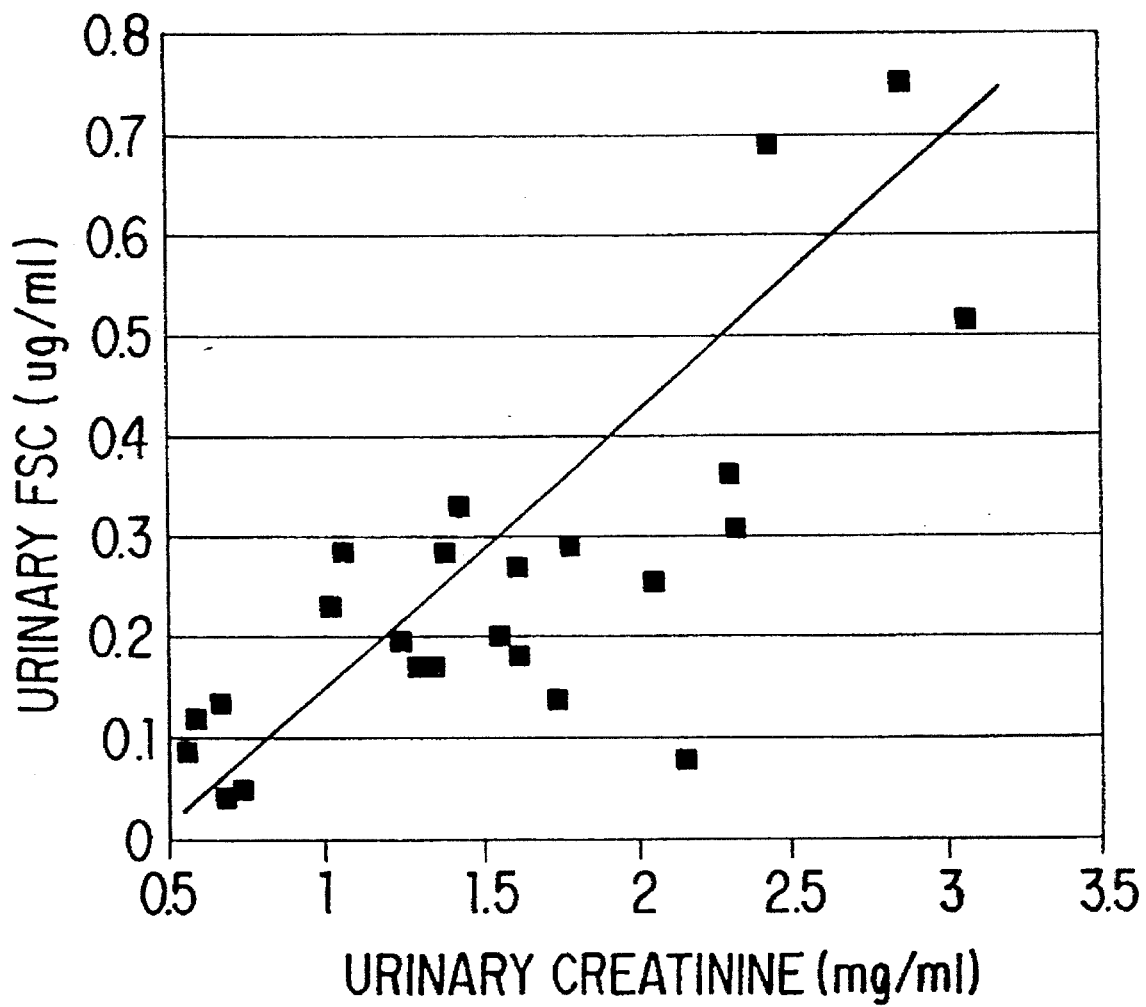
FIG. 2: Relationship between urinary FSC and creatinine. This regression analysis indicates the value of normalizing the data as FSC/creatinine. This ratio is calculated so as to increase the reliability and fidelity of the test results, as much as the variability of the values are due to the characteristic concentration level of the urine obtained from the animal. The correlation coefficient for creatinine ($r^2$ for creatinine vs. FSC) is 0.65.

The present invention provides for a surprisingly sensitive method useful in the early detection of organ rejection episodes in an animal. Particularly, the present methods are based on the rapid and sensitive quantification of glycoprotein free secretory component (FSC, also termed "secretory component of IgA" and "polymeric immunoglobulin receptor") in a biological sample. While this particular glycoprotein may be measured in a variety of different biological fluids, those biological fluids found most easily adaptable for use in the present methods included urine, amniotic fluid, bile, bronchial secretions and serum. Most preferably, the disclosed methods are used to measure FSC concentrations in a urine sample obtained from the animal being tested.

The present invention may be used to monitor and detect rejection of a single organ, or even the rejection of more than one organ, for example in patients who have received more than one type of organ transplant. However, those applications of the invention most preferred are drawn to methods for monitoring the rejection of a kidney transplant. By way of example, the presently disclosed methods may also be used to monitor liver, lung, pancreas or any combination thereof, in an animal. In one most particularly preferred embodiment, the method is used to monitor organ rejection in a human patient.

In the described method for identifying organ rejection in an animal, the method comprises the steps of obtaining a biological sample from the animal; measuring a concentration of free secretory component in the biological sample; comparing the concentration of free secretory component of the biological sample to a standard free secretory component concentration characteristic of a similar biological fluid. A standard FSC concentration may be obtained from samples obtained from non-organ transplant animals or from an animal which had received an organ transplant demonstrating normal transplanted organ functioning or from a sample obtained from the transplant animal (autologous) prior to a episode of organ rejection. Identification of an ongoing organ rejection, or the tissue damage which results from organ rejection (causes organ rejection in an animal), is determined in animals having a free secretary component concentration greater than a determined standard control free secretory component concentration characteristic of the biological fluid being measured.

A standard concentration of free secretory component concentration characteristic of a particular biological sample is determined by calculating the mean and 95% confidence interval of FSC concentration obtained from, for example, at least five age and sex-matched biological samples obtained from animals which had not received an organ transplant.

Most preferably, where the animal being monitored is a human, the reference population for determining control values most preferably includes at least 10 age and sex-matched animals. A 95% confidence interval is determined from the FSC concentrations determined from biological samples obtained from animals (for example, human subjects) in the reference population.

Alternatively, the free secretory component concentration characteristic of the biological sample to be used for comparative purposes may be the FSC concentration measured in an autologous sample before any rejection episode had occurred in the patient, or instead from an average FSC concentration measured for the patient after a rejection episode, but not during periods when the patient was experiencing a rejection episode. Alternatively, a mean and 95% confidence interval of FSC concentration may be calculated from a group of biological samples obtained from animals who had received an organ transplant but who had no prior evidence of an organ rejection episode.

Most preferably, the biological sample in which FSC is to be measured is a urine sample.

FSC levels have been observed to decrease rapidly in some renal transplant patients after their medicinal treatment has been changed. Therefore, the present invention may also be used in a method to conveniently and economically monitor a patient for the efficacy of an immunosuppressive agent regimen, which would concurrently indicate the status of the patients' renal transplant.

The present invention also provides a method for inhibiting a kidney transplant rejection in an animal. In a particular embodiment of the present invention, this method comprises the steps of obtaining a urine sample from the animal at subsequent periodic intervals after the kidney is transplanted; measuring free secretory component concentrations in each urine sample of the animal to provide test sample FSC concentrations; determining if the free secretory component concentration of the sample is elevated relative to a control free secretory component concentration; classifying an animal with an elevated concentration of urinary free secretory component as undergoing a kidney rejection episode; and treating the animal undergoing a kidney rejection episode with a regimen of immunosuppressive agents to prevent kidney rejection in the animal.

A similar method is provided in the present invention for identifying a renal allograft rejection episode in a kidney transplant patient. More specifically, the method for identifying a renal allograft rejection episode in a kidney transplant patient comprises: obtaining a patient urine sample from the transplant patient; determining the concentration of free secretory component in the patient urine sample to provide an FSC test concentration; determining an FSC urine control concentration from a population of at least 5 age and sex matched kidney transplant patients with no prior evidence of a kidney rejection episode; comparing the FSC urine control concentration to the FSC test concentration, wherein an FSC test concentration greater than the FSC concentration indicates a renal allograft rejection episode in the kidney transplant patient.

Most preferably, a patient urine sample is to be obtained before any signs of kidney rejection become evident. Additionally, frequent periodic urine specimens should be obtained and FSC measured from the kidney transplant patient as part of a comprehensive and effective monitoring system for the early detection of kidney transplant rejection.

Where the biological sample is a human urine sample, the control concentration of free secretory component in a non-kidney transplant human is about 1 µg/ml. While a variety of particular biochemical assays may be used to measure free secretory component in a biological sample, the assay most preferably used for this purpose is the modified ELISA (enzyme linked immunosorbent assay) described herein by the inventors (see Table 1).

Changes (i.e., an increase) in urine FSC levels are expected to occur relatively early in the organ rejection episode, and therefore the measurement of this particular glycoprotein provides for early detection of an incipient organ rejection episode, and further allows the physician to timely intervene to halt the ultimate rejection of the organ.

The specificity of the claimed invention for monitoring changes in the status of a transplanted kidney in an animal provides a definitive technique for distinguishing renal allograft rejection tissue injury from other forms of kidney injury, such as that manifest from cyclosporin toxicity. Most particularly this method comprises: obtaining a urine sample from the transplant recipient animal; determining an FSC concentration in the urine sample from the transplant recipient animal to provide an FSC test concentration; determining an FSC control concentration; and comparing the FSC test concentration to the FSC control concentration of, wherein an FSC test concentration greater than the FSC control concentration indicates a renal allograft rejection injury in the kidney transplant patient and wherein an FSC test concentration the same as or less than the FSC control concentration indicates a renal non-allograft injury.

The presently disclosed novel approach to monitoring organ rejection possesses the advantages of being economical, simple to administer, and noninvasive. The described method also offers a much more patient compatible alternative to other techniques currently practiced. The present methods also advantageously provide a method wherein renal allograft rejection may be specifically distinguished from other causes of kidney injury (e.g., cyclosporin toxicity). The specificity of the present inventive methods are thus unlike techniques which rely on biochemical measurement of serum components to monitor renal function or the excretion of other renal tubular and serum proteins of urine, including the $\beta$-2 microglobulin, $\gamma$-glutamyl trans-peptidase, acetyl-$\beta$-D-glucose aminidase, adenosine deaminase binding protein, the complement components, and lysozyme. Measurement of these substances do not distinguish kidney injury incident transplant rejection from other forms of kidney injury.

In that the inventors have also characterized changes in amniotic fluid content of FSC with the gestational age of the fetus, the present invention also provides a method for the early and accurate detection o fetal renal (kidney) dysfunction, as early as only 15 weeks gestation.

The present methods may also potentially be used to monitor for graft-versus-host disease in bone marrow transplants, again by measuring FSC in a biological fluid, most particularly, serum.

The present methods may be employed for monitoring renal diseases, particularly renal complications from urinary tract infection, including localized infection of the upper (pyelonephritis) and lower urinary tract (cystitis), interstitial nephritis, as well as congenital renal dysfunction in utero (through the measurement of FSC and amniotic fluid) employing secretory component as the indicating molecule. The present methods may also be used for detecting epithelial injury of other mucosal surfaces, such as that of the bronchial tubes (for detecting bronchitis) and the extent of lung injury (such as in cystic fibrosis) by quantifying secretory components in the serum or bronchial secretions.

The effective methods for monitoring the various conditions described herein are also employed in the description of a diagnostic kit which may be used for monitoring any of the above conditions, particularly for screening transplant recipients on a routine basis. Such constitutes a method superior to organ biopsy, which is currently considered the most definitive test available for the purpose of monitoring renal (kidney) rejection.

In a most preferred embodiment of the kit, for the detection of graft rejection in an animal, the kit comprises a carrier means adapted to receive at least one multiwell assay plate and at least three container means. The multiwell assay plate most preferably is coated with a polymeric immunoglobulin isolated from a human or other animal biological sample. The first container means most preferably comprises free secretory component. The second container means most preferably comprises an antibody to which an enzyme has been conjugated and having binding affinity specific for secretory component polymeric Ig complex. The third container means most preferably comprises a colorimetric substrate for the conjugated enzyme.

The antibody is most preferably a monoclonal antibody 6G11. Additionally, with regard to the most particularly preferred embodiments of the invention, the receptor ligand detection reagent is an anti-secretory component antibody bound to an enzyme. By way of example, the antibodies are bound to the enzyme horseradish peroxidase.

In a most preferred embodiment, the kit further includes a fourth container means comprising a diluent suitable for diluting a biological sample, an antibody or FSC. Such a diluent by way of example, is phosphate buffered saline. A fifth container means comprising a enzyme reaction buffer may also be included. By way of example, such an enzyme reaction buffer is could be a citrate buffer, particularly where the conjugated enzyme is horseradish peroxidase.

The described kit may also include a printed insert sheet with instructions for use of the kit in measuring the free secretory component concentration in an animal biological sample.

The following examples are presented only to describe preferred embodiments and utilities of the present invention and to satisfy best mode requirements. The examples are not intended to limit the scope of the present invention unless specifically indicated otherwise in the claims appended hereto. Thus, it is to be understood that other utilities and advantages and modifications of the specially described aspects of the present invention are embraced within the scope of the following claims.

Examples presented herein include:

Example 1—Assay for Free Secretory Component in a Biological Sample

Example 2—Free Secretory Component in Renal Transplant Patients

Example 3—Secretory Component in Amniotic Fluid to Detect Fetal Kidney Dysfunction Prophetic Proposed Comparative Study of Human Subject Study Example 4—of FSC Relevant to Age, Sex, Pathological Condition and Transplant Status Prophetic Proposed Diagnostic Kit for the Measurement of Example 5—Free Secretory Component Example 1

Assay for Free Secretory Component in a Biological Sample

The present example is provided to demonstrate the ELISA assay as modified and adapted by the inventors for the specific measurement of FSC in a biological sample, particularly for measurement of FSC in a voided urine sample obtained from a human. The object was to develop a simple, rapid and specific immunoassay for quantifying FSC in a representative biological fluid such as urine, which establishes the utility of employing the presently described method for measuring FSC in other biological samples, such as bile, bronchial secretions, amniotic fluid, and blood (particularly blood components such as serum).

The modified ELISA assay described herein will be used to standardize the urine baseline levels of FSC from human urine samples, and to quantify FSC concentrations in urine obtained from renal allograft recipients, most of whom may have been suspected of having had an episode of allograft rejection. A second object of the present example is to demonstrate a form of the modified ELISA assay which could be used in commercial application for measuring urinary FSC concentrations in the private clinical laboratory or hospital for early detection of renal transplant rejection.

The assay for measuring FSC in a biological fluid (which also may contain secretory component bound to immunoglobulins, such as secretory IgA and IgM) used in the present invention is a modified sandwich-type enzyme linked immunosorbent assay (ELISA) specifically adapted for the purpose of measuring FSC. The modified ELISA included the steps outlined in Table 1.

In this quantitative ELISA, free SC is captured on dimeric IgA coated wells. A major advantage of this assay system is its binding specificity for free SC, since SC already bound to IgA (sIgA) will not bind to dimeric IgA[18]. Using free SC purified from human milk as a standard[35,] this assay can be used to quantify the free SC content of virtually any biologic fluid.

The FSC immunoassay, according to the present example, may also be used to determine if a spot urine collection (in which FSC quantification results are normalized to the concentration of creatinine in the sample), can substitute for a timed urine sample in quantifying the FSC excretion rate. Adult urine samples were collected randomly from normal (i.e., non-transplant recipient) donors. Briefly, the modified ELISA protocol developed in the present. example, as used in preferred embodiments of the present invention, is described as follows:

ELISA Procedure for Clinical Patient Samples

Coating the Plates

1. Coat round bottom 96-well microliter plate with 150 µl/well IgM diluted to 3 µg/ml in 0.125M (pH 8.2) borate saline buffer. Coat all wells except row "A", this row is left as an O-coat control In row "A", fill wells with 150 µl/well borate saline buffer.

2. Cover the plate with sealing tape and incubate the plate in a 37° C. dry incubator overnight.

3. After the incubation period the plate, still sealed with tape, can be stored at 4° C. and used in the presently described assay for up to 6 months.

Addition of Free Secretory Component

1. Wash plate 8 times with Tween-saline to remove any non-bound antigen. Blot the plate on aL paper towel, checking to be sure all liquid and air bubbles are removed.

2. Fill all 96 wells with 150 µl Tween phosphate buffered saline (0.05M, pH 7.1). Each sample (e.g., urine sample) is assayed in duplicate and in "coated" wells and added to at least one "uncoated" control well. This is done as a background check. In each test well, 50 µl of sample is added to the 150 µl of buffer. The solution in each well is mixed by pipetting up and down 7–8 times without causing air bubbles. Draw out 50 µl from the control well and discard so that this well will not contain a 1:4 dilution. In the row B wells, add 50 µl of sample. Mix well, draw out 50 µl, and transfer to row C. Mix the contents of these wells thoroughly, and transfer 50 µl to the next row. Continue the above through row G, at which point 50 µl will be removed and discarded. Row H contains only Tween PBS; these wells are zero sample controls. The final volume of each well is 150 µl. FSC standard is diluted to a concentration of 2 µl/ml with Tween PBS and treated exactly as the samples.

3. Place a plastic lid over the plate and incubate at room temperature, with shaking, for 4 hours.

Addition of Antibody (Conjugate)

1. Wash plate 8 times with Tween saline.

2. Dilute conjugate in Tween PBS. Prepare rabbit anti-human secretory component horseradish peroxidase (conjugate) at a 1:200 dilution.

3. Add 150 µl of diluted conjugate to all 96 wells.

4. Incubate at room temperature, with shaking, for 4 hours.

Enzyme Reaction

1. Wash plate about 8 times with Tween saline.

2. For a horseradish peroxidase conjugate—Mix O-phenylenediamine dihydrochloride with citrate buffer (0.05M, pH 4.9) (0.2 mg OPD for every 1 ml of citrate buffer.) Add 3% Hydrogen Peroxide (50 µl $H_2O_2$ for every 20 ml citrate buffer). Add 150 µl of above substrate to all 96 wells, starting with row A and working down to row H. Time the reaction and watch for a color change (from clear to bright yellow). Stop the reaction by adding 50 µl of 5N $H_2SO_4$ to all 96 wells in the same sequence as addition of substrate.

3. Read plates on Dynatech ELISA reader. Be sure the wavelengths on the reader are set for the selected "conjugate" used in the assay (for example, set at wavelength 490 nm when horseradish peroxidase is used as the conjugate).

4. Graph data on 4 cycle semi-log paper Primary Antibody Dilution vs. OD per 100 minutes.

5. Calculate the concentrations of free SC in samples from the absorbance curve of sample and the standard. The free SC concentrations are reported as the average of the duplicate determinations.

TABLE 1

Modified ELISA for Quantifying Free Secretory Component.

| Plate or Surface | |
|---|---|
| pIgA or IgM | Surface of a plastic vessel or wells of a polystyrene microtiter plate are coated with human polymeric IgA, or IgM or monoclonal antibody 6G11 specific for FSC |
| → IgA | Unbound IgA removed by washing |
| + FSC | Add source of FSC |
| pIgA-FSC | Add biological sample (e.g. urine) or purified secretory component standard and allow to bind to the polymeric IgM or IgA coat (4 hr. incubation at 25° C.). |
| → | Unbound material removed by washing |
| | Add detecting antibody - |
| + Anti-SC-Enzyme pIgA-FSC-Anti-SC-Enzyme | Polyclonal or monoclonal antibodies against secretory component of sIgA, conjugated with horseradish peroxidase, is added (4 hr. incubation period at 25° C. |
| → | Unbound conjugate is removed by washing with 0.05% Tween phosphate buffered saline |

TABLE 1-continued

Modified ELISA for Quantifying
Free Secretory Component.

+ substrate
↓
pIgA FSC Anti-SC-Enzyme
↓
Colored product
↓
Read plates under ELISA
reader @ 490 nM wavelength Add colorimetric substrate (e.g.
0.2 mg/ml O-phenylenediamine
dihydrochloride in citrate buffer)

Stop reaction with sulfuric acid
The enzyme bound to the
tube is quantified using
a colorimetric substrate
and spectrophotometry Creatinine is quantified from an aliquot of the same urine sample by standard techniques. The results are expressed as micrograms (μg) of FSC per milligram (mg) of creatinine.

Using the foregoing described modified ELISA, the FSC/creatinine ratio for nonpregnant adults was determined to be approximately 1.04 μg FSC/mg creatinine (Range 0.19–3.38). Two pregnant adults demonstrated a mean free secretory component concentration approximately three times the amount of a non-pregnant adult.

The mean FSC urine concentration of the renal transplant patient was 18 μg secretory component/mg of creatinine (Range 0–137 mg). Twelve of the 20 patients had levels above the range of normal subjects on at least one of their tests.

Table 3 presents average FSC concentrations characteristic of different biological samples, such as adult urine (1.18±0.91), adult parotid fluid (6.61±4), adult bile (7.49±9.8) and human milk (1990±531).

TABLE 2

Concentrations of free SC in
amniotic fluid compared with that of other secretions
Free SC Content (μg/ml)

| Secretion | Number of Samples | Mean | S.D. |
|---|---|---|---|
| Amniotic fluid | 25 | 7.45 | 7.04 |
| Neonatal Urine | 7 | 6.79 | 3.45 |
| Adult Urine | 13 | 1.18 | 0.91 |
| Adult Parotid Fluid | 9 | 6.61 | 4.00 |
| Adult Bile | 5 | 7.49 | 9.80 |
| Adult Milk | 5 | 1990 | 531 |

The term "modified" is used in the presently described protocol, a human immunoglobulin (IgM or polymeric IgA) is used as the first "capture" phase of the assay. This binds FSC as a ligand receptor complex, not as an antibody. In most ELISA's the "capture" reagent is an animal antibody to the analyte (analyte is FSC, in this case).

An antibody having binding affinity specific for FSC may be substituted for polymeric immunoglobulin as the capture reagent in the practice of the present assay for measuring FSC. An antibody most preferred in the practice of the present invention is the monoclonal antibody, 6G11, which is highly specific for FSC. This antibody most preferably may be added to a microliter well dilute to an appropriate concentration in a buffer, such as 10 mM phosphate buffered (or borate buffered) saline, pH 7.4. The 6G11-coated wells are then employed to measure FSC concentrate in biological samples from non-organ transplant and organ t patients.

Most preferably, human serum products are to be used in the practice the present assay. Various reagents known to stabilize antibodies absorbed to a solid phase may also be used in the practice of the presently described assay in order to allow the plates to be stored dry. The stabilizing reagents which are planned for use in the described assay include various concentrations of sugars, gelatins, or buffers, such as 0.1M sodium phosphate, pH 7.4.

A secondary (monoclonal or polyclonal) antibody (i.e., a receptor ligand detecting reagent), specific for sIgA, SC and FSC is used in the practice of the present invention. These secondary antibodies are characterized by their ability to bind to epitopes distinct from the ones recognized by polymeric IgA or monoclonal 6G11. Most preferably, the antibodies employed in the described assay are purified by affinity chromatography on staphylococcal protein A and conjugated to horseradish peroxidase by a modification of the Nakane et al. procedure[31].

The presently described ELISA for FSC is relatively free of cross-reactivity to sIgA, IgG, IgM, cyclosporin and antibiotics. Therefore, these substances are expected by the inventors to have relatively no effect on the assay value of the sample FSC concentration obtained according to the presently described method. The sensitivity of the described ELISA assay is currently about 10 ng/ml FSC for detecting FSC in a biological sample of urine.

The following table presents control values for FSC urine samples as obtained from a population of 10 normal (non-allograft) human subjects using the modified ELISA assay described herein. Creatinine measurements were obtained according the procedure described by Jaffe[41].

TABLE 3

Rodney's Normal Values for FSC

| Subjects | FSC μg/ml | Creat mg/ml | FSC/Creat μg/mg |
|---|---|---|---|
| 1 | 0.089 | 0.56 | 0.159 |
| 2 | 0.285 | 1.06 | 0.269 |
| 3 | 0.330 | 1.43 | 0.231 |
| 4 | 0.135 | 0.67 | 0.201 |
| 5 | 0.120 | 0.59 | 0.203 |
| 6 | 0.195 | 1.24 | 0.157 |
| 7 | 0.180 | 1.61 | 0.112 |
| 8 | 0.750 | 2.87 | 0.261 |
| 9 | 0.285 | 1.38 | 0.207 |
| 10 | 0.690 | 2.44 | 0.283 |
| Mean | 0.306 | 1.385 | 0.208 |
| STD | 0.220 | 0.729 | 0.052 |
| C.V. | 0.720 | 0.527 | 0.249 |

The data of Table 3 presents concentrations of FSC and FSC/creatinine measured by the inventors employing the modified ELISA protocol described at Table 1. The mean FSC concentration observed was 0.306 μg/ml±0.220. Corrected for creatinine concentration (mg/ml), the sample readings yielded a mean of 0.208±0.052 μg FSC/mg creatinine.

Example 2

Free Secretory Component in Renal Transplant Patients

The present example provides the range of FSC level observed in adult renal transplant patient urine samples. These results support the correlation between elevated urinary FSC excretion and the incidence of allograft (kidney) rejection, and are submitted to demonstrate the utility of employing patient FSC concentration in a method for identifying graft rejection in an animal.

In this study, 20 consecutive patients admitted to a medical transplant unit for suspected renal allograft rejection or other complaints were tested each weekday morning for FSC excretion. Normal urine was collected from laboratory personnel (no history of organ transplant) to provide control values. FSC was quantified in the fresh urine samples using the modified sandwich-type ELISA developed in the inventors' laboratory (see Table 1, Example 1). The results were normalized for urinary creatinine concentration. The histologic diagnosis of 11 of these patients was established by an independent (blinded) review of the renal biopsies by the inventors. The data obtained from the 11 patients whose diagnosis was established by renal biopsy in this study is included in Table 4.

TABLE 4

Urinary Free Secretory Component in Renal Transplant Patients

| Patient Number | FSC μg/ml | Creatinine mg/ml | FSC/Creat | Biopsy Results |
|---|---|---|---|---|
| Patients with biopsy evidence of renal allograft rejection: | | | | |
| 1 | 0.8–18.0* | 0.19–0.33 | 0–94.9 | Severe Rejection |
| 7 | 9.3–36.8 | 0.3–0.99 | 15.6–49.1 | Mild Rejection |
| 9 | 56.4 | 0.41 | 137.6 | A & C Rejection |
| 14 | 2.4–10.8 | 1.4–1.9 | 1.7–5.7 | Mild Rejection |
| 16 | 5.3 | 0.46 | 11.5 | Chronic Rejection |
| 2 | 1.1–2.5 | 0.84–0.87 | 1.3–3.0 | Chronic Rejection |
| Patients with no evidence of rejection on biopsy: | | | | |
| 4 | 6.2–13.6 | 0.42–1.4 | 4.5–26.2 | CSA Toxicity |
| 3 | 0.7 | 0.64 | 1.1 | ATN |
| 5 | 0.0 | 0.41 | 0.0 | ATN |
| 11 | 0.0–2.5 | 0.08–0.27 | 0.0–16.0 | Throm Microangiopathy |
| 13 | 0.0 | 0.32–0.4 | 0.0 | Chronic CSA Toxicity |
| Normal adult values (N = 15) | | | | |
| Mean | 1.16 | 1.03 | 1.09 | |
| Std Dev | 1.4 | 0.63 | 0.79 | |
| Range | 0.21–3.12 | 0.32–2.45 | 0.19–3.38 | |

*Range of values during a single hospitalization (1–9 per patient). In many cases immunosuppressive medications were altered during the hospitalization.
A & C = acute & chronic; ATN = acute tubular necrosis; Throm = thrombotic; CSA = cyclosporin A.

The FSC concentration and FSC/creatinine ratio in the transplant recipients were frequently much higher than those in the normal subjects. More specifically, concentrations of urinary FSC were generally higher in the patients with biopsy evidence of allograft rejection, compared to transplant patients with no evidence of rejection on biopsy. One out of the five patients whose renal biopsy did not show rejection did have elevated levels of FSC (Patient No. 4—Table 4). However, this patient was judged to be having graft rejection on the basis of clinical findings and routine laboratory tests, suggesting that the biopsy might have been done before the pathologic findings became diagnostic of rejection. In contrast, all of the patients who had renal biopsy evidence of organ (kidney) rejection also had increased urine FSC concentration detectable at some point during their hospitalization.

The FSC data on patients who did not have renal biopsies seemed to follow the same general pattern (i.e., generally lower FSC/creatinine ratios).

Preliminary correlations of the urinary FSC values with clinical and laboratory indicators of renal graft rejection for the entire group (with an without biopsy) revealed that of 8 patients who the clinician thought to be undergoing renal allograft rejection, 7 had a FSC/creatinine ratio of greater than 5 μg FSC/mg of creatinine in at least one sampling specimen. Of the eight patients who were not thought to have allograft rejection or infection, only 2 had a level of above 5 μg FSC/mg creatinine (25%) false positive rate. One renal transplant recipient who was admitted for control of his hypertension (a recognized sign of renal allograft rejection) also had high FSC levels in all of his urine samples collected.

The mean FSC level in the urine of the whole group of renal transplant patients (admitted because of suspected rejection) was 18 g FSC/mg of creatinine (Range 0–137 μg/mg). Twelve (12) of the twenty (20) patients had levels above the range of the determined "normal" subjects in at least one of the sample specimens collected. Four (4) patients had FSC levels below detectability in at least one of the sample specimens collected, while six demonstrated FSC levels consistently within the range of the normal subjects.

These results demonstrate that the level of FSC in a patient sample is a reliable indicator of kidney injury caused by allograft rejection. The presently disclosed methods therefore provide a useful clinical tool for screening organ transplant recipients to detect early organ transplant rejection. Additionally, monitoring for elevated FSC levels in urine could be used to alert the physician to the need for further testing, and possibly treatment of the transplant patient to prevent and/or halt an ongoing organ rejection episode.

Example 3

Secretory Component Amniotic Fluid to Detect Fetal Kidney Dysfunction

The present example is provided to demonstrate the utility of the claimed invention for the detection of kidney dysfunction in a fetus, and the diagnostic value of measuring FSC in amniotic fluid for identifying fetal renal dysfunction. The inventors propose that these methods will have utility for the detection of Potter's syndrome, a condition characterized by abnormal fetal kidney development. According to the techniques disclosed for the present invention, conditions such as Potter's syndrome may be monitored and detected in the unborn child by obtaining a sample of the amniotic fluid which surrounds the fetus. This amniotic fluid sample may then be measured for free secretory component (FSC) using the modified ELISA methods described herein.

The vast majority of AmF volume is derived from fetal urine, especially during the later half of pregnancy.[36] Since adult urine is known to contain low levels of sIgA,[37] a potential source for the free SC was proposed by the present inventors in AmF.

Results presented in the present example indicate that most of the secretory component (SC) in human amniotic fluid (AmF) exists in its free form. The inventors also show that SC concentration in AmF will vary in concentration directly with the gestational age of the fetus. The free SC is also shown to migrate at a slightly larger apparent molecular weight on SDS-PAGE.

Amniotic fluid samples were obtained from pregnant females according to techniques well known for this process by those of skill in the obstetrical medical arts. In the present example, free SC was quantified in amniotic fluid samples obtained from term amniocenteses (37–40 weeks gestation)

(See Table 2 supra) as well as from amniocenteses of earlier gestational pregnancies.

Effect of gestational age on free SC concentration in AmF.

The concentration of FSC relative to gestational age was examined. The modified ELISA assay described in Example 1 was employed to measure FSC in the amniotic fluid samples.

FIG. 1 is a scatter plot of the concentrations of free SC in 50 AmF samples collected at various gestational ages. The concentration of free SC in AmF appears to be directly related to the gestational age of the fetus, especially between 26–40 weeks gestational age. While SC concentration varied in samples of similar gestational ages, substantial quantities of free SC were found in all samples from pregnancies of greater than 21 weeks duration, and free SC was detected in two of the three samples from the earliest stage of gestation (16 weeks) tested. The concentration of free SC began to rise steadily after 26 weeks, and at term, free SC levels ranged from 2–28 µg/ml.

The difficulty associated with obtaining specimens early in gestation prevents a determination of the exact relationship between free SC and gestational age. However, a simple linear regression between the concentration of SC and gestational age between 26 to 40 weeks yielded a line with a slope of 0.692, a correlation coefficient of 0.374, and a p value of 0.014 (two tailed T test), indicating that free SC concentrations in AmF increase with gestational3- age from between 26 to 40 weeks.

The free SC concentration of AmF samples (38–40 weeks) was compared to that in the first voided urine of newborn infants and various other secretions (adult urine, parotid fluid, bile, and milk) in Table 2. These results show that the free SC concentration in AmF is similar to that found in neonatal urine, but both are higher than concentrations found in random adult urine (See Table 2). The concentration of free SC in AmF was also similar to concentrations found in bile and parotid fluid. In contrast, the concentration of free SC in milk was much higher than in AmF or other secretions.

In a particularly preferred embodiment of the prenatal diagnosis aspect of the invention, FSC is to be measured in amniotic fluid obtained from pregnant females wherein the fetus is of at least 21 weeks gestation. A concentration of FSC from a pregnant animal which is significantly lower than a control FSC concentration in AmF obtained from a similar gestational pregnancy would indicate a fetus at risk of having renal dysfunction.

Prophetic Example 5

Proposed Comparative FBC Study of Human Subjects Relative to Age, Sex, Pathological Condition and Transplant Status The present prophetic example is provided to outline a proposed comparative study to determine a baseline or "normal" secretory component concentration level from patients in various physiological states (young, old, transplanted w/disease, transplanted w/o disease, pregnant, non-pregnant) as well as between the sexes (male vs. female). Evaluation of relative elevated or decreased free SC levels in a transplant patient or pregnant female patient may then be compared with the distribution of FSC concentrations defined for these populations. Additionally, the proposed study will provide data which may aid in the development of therapeutic products for treating individual kidney transplant patients.

A number of different subject populations will be studied in the proposed project. In each case, the subject will be asked to provide single or multiple voided urine samples. The populations proposed for study are listed below:

| Health Status | Number | Age Range | Sex | Ethnic |
|---|---|---|---|---|
| a. Normal adults and children | 30 | 4–90 yrs | M & F | Mixed |
| b. Pregnant females | 10 | 18–40 yrs | F | Mixed |
| c. Acute pyelonephritis | 10 | 4–90 yrs | M & F | Mixed |
| d. Bacterial pneumonia | 10 | 4–90 yrs | M & F | Mixed |
| e. Active rheumatic disease | 10 | 4–90 yrs | M & F | Mixed |
| f. Kidney transplant recipients with no signs of rejection | 20 | 4–90 yrs | M & F | Mixed |
| g. Patients other than transplant recipients receiving cyclosporin | 10 | 14–90 yrs | M & F | Mixed |

The inclusion and exclusion criteria to be applied in the present study are solely related to the subject's health status and the particular patients ability to reliably provide a urine sample. Where the patient population being tested are females, the women will be tested during each phase of their menstrual cycle.

Pregnant females will be considered separately. This group of females will be considered separately because evidence in the literature that female sex hormones. (i.e., estrogen) alter the production of SC[24].

Results from this proposed study will provide estimates of the means and confidence limits for FSC concentration for each of the populations of: normal adult males; normal adult females (non-pregnant); pregnant females; children; transplant recipients not demonstrating an organ-rejection episode; patients with kidney infection or other infections and generalized inflammation; and patients receiving cyclosporin independent of kidney transplantation. These baseline reference population FSC concentrations will then be employed for identifying allograft rejection in a patient using the reference population most similar to the test subject animal.

Prophetic Example 6

Proposed Diagnostic Kit for the Measurement of Free Secretory Component

The present example is provided to demonstrate a preferred embodiment contemplated by the inventors for a diagnostic kit to be used to monitor patients for organ transplant rejection. The kit is also expected to have diagnostic utility for monitoring and detecting other forms of kidney inflammation in the patient's own kidney. In addition the proposed kit may be used for detecting fetal renal dysfunction in a pregnant animal, such as fetal Potter's syndrome, using, for example, an amniotic fluid sample.

The kit comprises a carrier means adapted to receive at least one multiwell assay plate and at least three container means in close confinement therewith; at least one multiwell assay plate; a first container means comprising free secretory component; a second container means comprising an enzyme conjugated antibody capable of binding to the receptor (secretory component) ligand (polymeric Ig) complex; and a third container means containing a colorimetric substrate for the enzyme.

The kit may also include a fourth container means comprising an appropriate diluent for the antibody, FSC or sample, such as for example phosphate buffered saline. The kit may also further include fifth container mean containing an enzyme reaction buffer. By way of example, an enzyme reaction buffer is citrate bugger, particularly where the conjugated enzyme is horseradish peroxidase.

It is contemplated that the described kit will be widely applicable for use in hospitals and private clinical laboratories, for the detection of either single graft rejections or multi-transplant organ rejection (i.e., where the patient has had multiple organ transplants) episodes in patients.

The carrier means will most preferably be constructed of a durable plastic material.

The presently described diagnostic kits may also optionally comprise a multiwell microliter plate which is pre-coated with an appropriate concentration of a monoclonal antibody to FSC, and a pamphlet of written instructions for use of the kit. In a most preferred embodiment of the described kit, the antibody is the monoclonal antibody 6G11. The antibody and the hybridoma which produces the monoclonal antibody is maintained in the inventors laboratory at the following address:
Dr. Randall Goldblum
Department of Pediatrics
The University of Texas Medical Branch, Galveston, Tex.

Most preferably, the ligand capture reagent is a polymeric immunoglobulin, such as pIgA or IgM.

A suitable urine or urine-like solution will be developed to provide acceptable stability of FSC standards to be used where the test sample is a voided human urine sample. Free secretory component (FSC) purified from human breast milk will be used to prepare standards in a matrix that approximates that of urine. If FSC is not sufficiently stable in urine or a urine-like solution, stabilizers and bulking agents, such as gelatin, etc., may be added to the solution to enhance stability of the FSC in solution.

Stabilizers and bulking agents, such as gelatin, etc., may be added to the solution to enhance the stability of the FSC in solution, such as in a solution of urine.

The following references, in pertinent part, are specifically incorporated herein by reference for the purposes indicated herein.

BIBLIOGRAPHY

1. Acher et al. (1979), *Transplantation*, 28:172.
2. Cosimi et al. (1981), *N. Engl. J. Med.*, 305:308.
3. Colvin et al. (1987), *Clin. Immunol. Immnopathol.*, 43: 273–276.
4. Tomasi, T. B. (1976), *In The Immune System of Secretions* Prentice-Hall, Prentice-Hall, Englewood Cliffs, N.J., p. 45.
5. Hart et al . (1983), *J. Clin. Lab. Immunol.*, 12:17.
6. Edward et al. (1983), *Kidney Int.*, 23:767.
7. Ward, J. P., (1976), *Br. J. Urol.*, 47:765.
8. Whiting et al. (1980), *Clin. Chem. Acta.*, 108:1.
9. Whiting et al. (1983), *Clin. Chem. Acta.*, 130:369.
10. Dyck et al. (1979), *Clin. Chem. Acta.*, 91:111.
11. Tolkoff-Rubin et al. (1986), *Tansplantation*, 41:593.
12. Tomasi, T. B., Jr., (1968), *Adv. Immunol.*, 9:1.
13. Tourville, D. R., Adler, R. H., Bienenstock, J., Tomasi, T. B., Jr. (1976), *J. Exp. Med.*, 121:101.
14. Mostov, K. E. Kraehenbuhl, J. P., Blobel G. (1980), *Proc. Natl. Acad. Sci. USA*, 77:7257.
15. Brandtzaeg, P. (1978), *Scand. J. Immunol.*, 8:39
16. Weicker J., Underdown B. J. (1975), *J. Immunol.*, 114:1137.
17. Crago, S. S., Kulhavy R., Prince, S. J., Mestecky, J. (1978), *J. Exp. Med.*, 147:1832.
18. Kuhn, L. C., Kraehenbuhl, J. P. (1979), *J. Biol. Chem.*, 254:11072.
19. Kuhn, L. C., Kraehenbuhl, J. P. (1982), *J. Biol. Chem.*, 256:12490.
20. Mostov, K. E., Blobel, G. (1982), *J. Biol. Chem.*, 257:11816.
21. Kuhn, L. C., Kraehenbuhl, J. P. (1982), *Trends Biochem. Res.*, 7:299.
22. Svanborg-Eden, C. (1979), *Infect. and Immun.*, 22:790-797.
23. Tomasi, T. B. (1976), *The immune system of secretions*, Englewood Cliffs, Prentice-Hall.
24. Sullivan, D. A., Richardson, G. S., MacLaughlin, D. T., Wira, C. R. (1984 ), *J. Steroid Biochem.*, 20: 509-13.
25. Sollid, L. M., Kvale, D., Brandtzaeg, P., Markussen, G., Thorsby, E. (1987), *J. Immunol.*, 138:4303.
26. Kvale, D., Brandtzaeg, P. and Lovhaug (1988), *Scand. J. Immunol.* , 28:351.
27. Phillips, J. O., Everson, M. P., Moldoveanu, Z., Lue, C., and Mestecky, J. (ed.) *J. Immunol.*, 145:1740–1744.
28. Abramowsky, C. R., Swinehart, B. A. (1986), *Am. J. Pathol.*, 125:571–577.
29. Marx, M., Weber, M., Schafranek, D., Wandel, E., Meyer Zum Buschenfelde K–H, Kohler, H. (1989), *Clin. Immunol. Immunopath.*, 53:181.
30. Woodard, C. S., Splawski, J. B. Goldblum, R. M., Denney, R. M. (1984), J. Immunol., 133:2116.
31. Nakane, P. K., Kawaci, A. (1974), *J. Histochem. Cytochem.*, 22 (12): 1084–1091.
32. Floegl et al. (1990),, Nephron, 56: 50–55.
33. Mellander et al. (1986), *Clin. Exp. Immunol.*, 63:555.
34. Laemmli, U. K. (1970), *Nature,* 227:680.
35. Mach, J. P. (1970), *Nature,* 228:1278.
36. Lotgering et al. (1986), *Semin. Perionatol.*, 10:94.
37. Fliedner et al. (1986), *J. Pediatr.,* 109:416.
38. Bakos et al. (1991), *J. Immunol.*, 146:162–168.
39. Brandtzaeg, P. (1977), *Immunochemistry,* 14:179.
40. Yoshida et al. (1985), *Am. J. Gastroenterol.*, 80:237.
41. Jaffe, M. Z. (1986), J. Physiol. Chem., 10:391.

What is claimed is:

1. A method for inhibiting a kidney transplant rejection in an animal with a kidney transplant comprising:

obtaining a urine sample from the animal at periodic intervals after the kidney is transplanted;

measuring FSC concentrations in each urine sample of the animal to provide FSC test concentrations;

determining an FSC control urine concentration;

identifying an elevated FSC test concentration in a test sample having an FSC concentration greater than the FSC control urine concentration as determined by an immunological method;

employing said elevated FSC test, concentration as an aid in identifying an animal undergoing a kidney rejection episode; and treating the animal undergoing a kidney rejection episode with a regimen of immunosuppressive agents to inhibit kidney rejection in the animal.

2. A method for aiding in identifying a renal allograft rejection episode in a kidney transplant patient comprising:

obtaining a urine sample from the transplant patient;

determining the concentration of FSC in the patient urine sample to provide an FSC test concentration;

determining an FSC urine control concentration;

comparing the FSC test concentration to the FSC control concentration; and identifying a renal allograft rejection episode in the kidney transplant patient when an FSC test concentration is greater than the FSC control concentration as determined by an immunological method.

3. The method of claim 1 or 2 wherein the FSC concentration of a urine test sample is determined by an enzyme linked immunosorbent assay.

4. The method of claim 1 or 2 wherein the FSC control concentration is about 1 µg/ml as determined by an immunological method.

5. The method of claim 1 or 2 wherein the FSC control concentration and the FSC test concentration are normalized as against a creatinine concentration of the biological sample.

6. A method for aiding in distinguishing renal allograft rejection injury from renal non-allograft injury in a kidney transplant patient comprising:

obtaining a urine sample from the kidney transplant patient with a form of kidney injury;

determining a FSC concentration in the patient urine sample to provide an FSC test concentration;

determining an FSC control concentration from urine sample obtained from non-kidney transplant patients; and comparing the FSC test concentration to the FSC control concentration as determined by an immunological method;

wherein an FSC test concentration greater than the FSC control concentration indicates s renal allograft rejection injury in the kidney transplant patient and wherein an FSC test concentration the same as or less than the FSC control concentration indicates renal non-allograft injury.

7. The method of claim 6 wherein a form of kidney injury is identified in a kidney transplant patient having an elevated level of a marker selected from the group consisting of gamma glutamyl trans-peptidase; N-acetyl-β-D-glucosaminidase; adenosine deaminase-binding protein; complement component; and lysozyme.

8. The method of claim 6 wherein the FSC test concentration and the FSC control concentration are normalized against a creatinine concentration of the urine sample.

9. A method for identifying renal inflammation in an animal not having a kidney transplant comprising:

obtaining a urine sample from the animal;

determining the FSC concentration in the animal urine sample by an immunological method to provide an FSC test concentration;

determining an FSC control concentration by an immunological method; and comparing the FSC test concentration to the FSC control concentration;

wherein an FSC test concentration greater than the FSC control concentration indicates renal inflammation in the animal.

10. The method of claim 9 wherein the animal is a human.

11. The method of claim 9 wherein renal inflammation is renal infection or renal tubular inflammatory injury.

12. A kit for use in the identification of an ongoing kidney graft rejection in an organ in an animal comprising:

a carrier means adapted to receive at least one multi-well assay plate and at least three container means;

at least one multi-well assay plate coated with a binding member polymeric IgA or IqM capable of specifically binding free secretory component;

a first container means comprising FSC;

a second container means comprising a detecting reagent of an enzyme conjugated-antibody, said antibody having binding affinity specific for secretory component-polymeric immunoglobulin complex; and a third container means comprising a colorimetric substrate for the enzyme.

13. The kit of claim 12 wherein the detecting reagent is an anti-secretory component antibody bound to an enzyme.

14. The kit of claim 13 wherein the FSC is isolated from human milk.

15. The kit of claim 12 which further includes a fourth container means having a diluent suitable for diluting a biological sample, the detecting reagent or FSC.

16. The kit of claim 15 which further includes a fifth container means having an enzyme reaction buffer.

17. The kit of claim 16 wherein the enzyme reaction buffer is a citrate buffer where the enzyme is a conjugated enzyme horseradish peroxidase.

* * * * *

UNITED STATES PATENT AND TRADEMARK OFFICE
CERTIFICATE OF CORRECTION

PATENT NO. : 5,484,707

DATED : January 16, 1996

INVENTOR(S) : Randall M. Goldblum and Srinivasan Rajaraman

It is certified that error appears in the above-identified patent and that said Letters Patent is hereby corrected as shown below:

In column 17, line 65, delete "t patients" and insert --transplant patients-- therefor.

In column 23, line 8 delete "bugger" and insert --buffer-- therfor.

Signed and Sealed this

Second Day of July, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,484,707
DATED : January 16, 1996
INVENTOR(S) : Randall M. Goldblum, *et al.*

It is certified that error appears in the above-indentified patent and that said Letters Patent is hereby corrected as shown below:

In Claim 1, Column 24, line 56, delete "," after "test".

In Claim 6, Column 25, line 33, replace "S" with --a--.

In Claim 12, Column 26, line 22, replace "IqM" with --IgM--.

Signed and Sealed this

Twenty-third Day of July, 1996

*Attest:*

BRUCE LEHMAN

*Attesting Officer*  *Commissioner of Patents and Trademarks*